United States Patent [19]

Vandewalle et al.

[11] Patent Number: 4,539,153
[45] Date of Patent: Sep. 3, 1985

[54] METHOD OF PREPARING 1 α-HYDROXYVITAMIN D AND 1 α-HYDROXYPREVITAMIN D COMPOUNDS, AND ADDUCTS OF A PREVITAMIN D OR TACHYSTEROL COMPOUND WITH A SUITABLE DIENOPHILE

[75] Inventors: Maurits Vandewalle; Luc J. Vanmaele; Pierre J. De Clercq, all of Gent, Belgium; Sebastianus J. Halkes; Wilhelmus R. M. Overbeek, both of Weesp, Netherlands

[73] Assignee: Duphar International Research B.V., Weesp, Netherlands

[21] Appl. No.: 636,782

[22] Filed: Jul. 31, 1984

Related U.S. Application Data

[63] Continuation of Ser. No. 399,251, Jul. 19, 1982, abandoned.

[30] Foreign Application Priority Data

Jul. 17, 1981 [NL] Netherlands ............... 8103393

[51] Int. Cl.³ .................................... C07J 9/00
[52] U.S. Cl. ..................................... 260/397.2
[58] Field of Search ........................... 260/397.2

[56] References Cited

U.S. PATENT DOCUMENTS

| | | | |
|---|---|---|---|
| 3,901,928 | 8/1975 | Hesse et al. | 260/397.2 |
| 4,022,768 | 5/1977 | Matsunaga et al. | 260/397.2 |
| 4,110,446 | 8/1978 | De Luca et al. | 260/397.2 |
| 4,202,829 | 5/1980 | De Luca et al. | 260/397.2 |
| 4,335,120 | 6/1982 | Holick et al. | 424/238 |

Primary Examiner—Elbert L. Roberts
Attorney, Agent, or Firm—Stevens, Davis, Miller & Mosher

[57] ABSTRACT

The invention relates to a method of preparing 1 α-hydroxyvitamin D or 1 α-hydroxy-previtamin D compounds by hydroxylating the 1 α-position of an adduct of a previtamin D compound with a suitable dienophile, in which adduct optionally present hydroxy group or hydroxy groups is or are protected, if desired, and after removal of the protecting group or groups, isolating the 1 α-hydroxyvitamin D or 1 α-hydroxy-previtamin D compound.

The invention also relates to 1 α-hydroxy-previtamin D compounds.

The invention further relates to an adduct of a previtamin D or tachysterol compound with a dienophile of the general formula

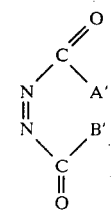

in which A' and B' are equal and represent methoxy groups or ethoxy groups, or in which A' and B' together constitute a phenylimino or o-phenylene group.

34 Claims, 1 Drawing Figure (I)

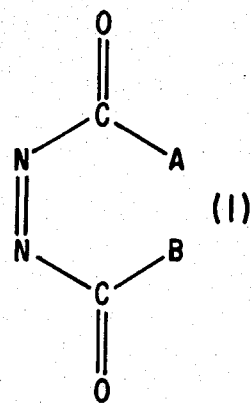
(1)
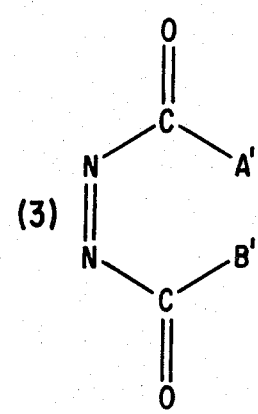
(3)
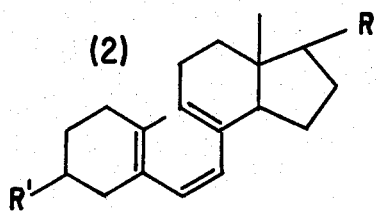
(2)
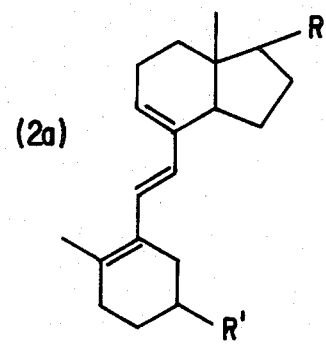
(2a)
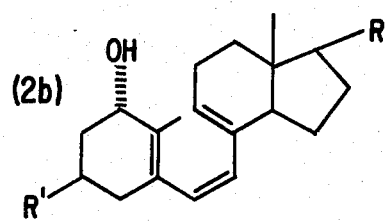
(2b)
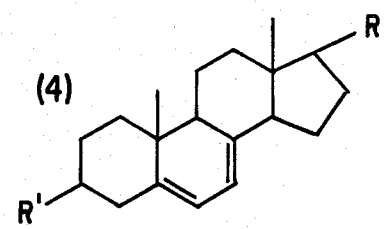
(4)
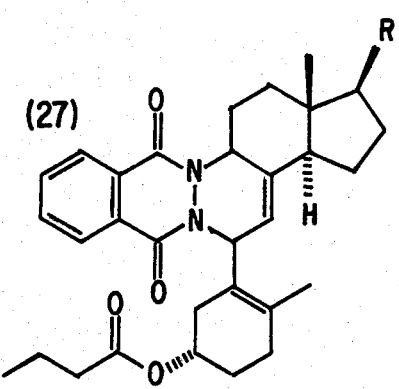
(27)
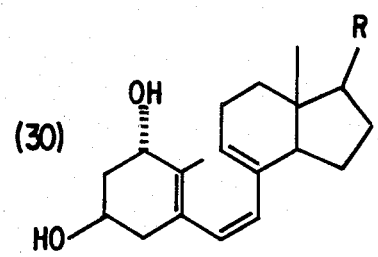
(30)

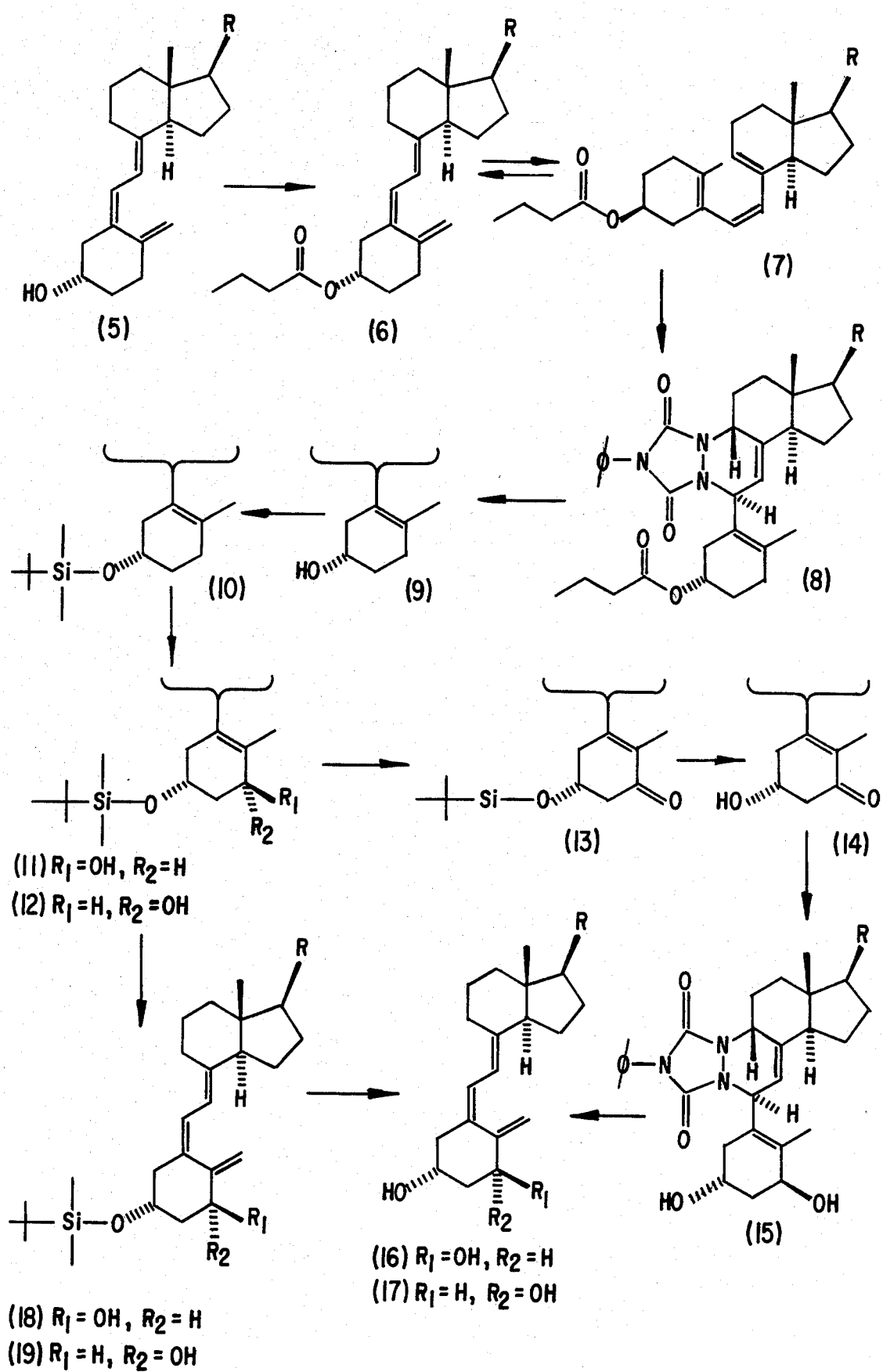

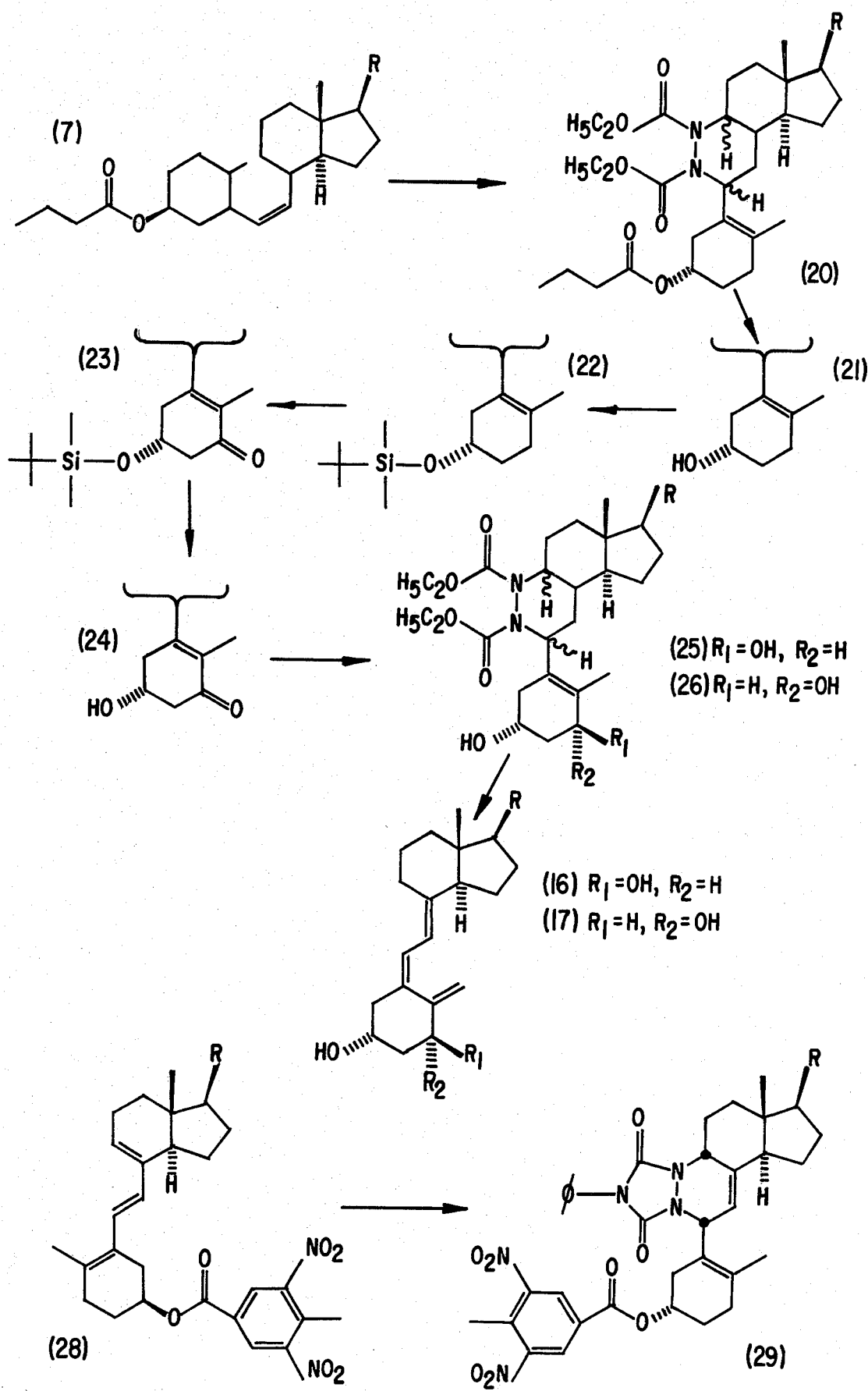

METHOD OF PREPARING 1 α-HYDROXYVITAMIN D AND 1 α-HYDROXYPREVITAMIN D COMPOUNDS, AND ADDUCTS OF A PREVITAMIN D OR TACHYSTEROL COMPOUND WITH A SUITABLE DIENOPHILE

This application is a continuation, of application Ser. No. 399,251, filed 7/19/82 now abandoned.

The present invention relates to the preparation of 1α-hydroxyvitamin D or 1α-hydroxy-previtamin D compounds and to adducts of a previtamin D or tachysterol compound with suitable dienophiles. The invention also relates to 1α-hydroxy-previtamin D compounds.

It is generally known that 1α-hydroxyvitamin D compounds, for example, 1α-hydroxyvitamin $D_3$, 1α,25-dihydroxyvitamin $D_3$ and 1α,24,25-trihydroxyvitamin $D_3$ have a strong biological activity and may be used in all those cases in which problems with the calcium metabolism play a role. In principle 1α-hydroxy-previtamin D compounds can be used for the same biological applications.

With a view to the great need of 1α-hydroxyvitamin D compounds, a good method of preparing these compounds is consequently of great importance.

Netherlands Patent Specification No. 159.093 discloses the preparation of 1α-hydroxyvitamin $D_3$ starting from cholesterol in approximately 15 reaction steps. According to the method described, a hydroxy group is introduced into the 1α-position prior to the UV-irradiation. This has for its disadvantage the fact that the yield of 1α-hydroxylated vitamin D compound obtained in the UV-irradiation is low, namely at most 20%, as compared with the yield in the UV-irradiation-step of a corresponding compound not hydroxylated in the 1-position; in the latter case a yield of 60% calculated on converted starting material can easily be obtained (see, for example, M. P. Rappoldt and E. Havinga, Recueil 79, p. 369 (1960)). Other reaction steps of the process described in the above-mentioned Netherlands Patent Specification also give a low yield.

A process of preparing 1α-hydroxyergocalciferol is also known from U.S. Pat. No. 3,907,843, in which, however, isoergosterone is used as a starting material. This process has the same above-mentioned disadvantages. Obviously, these disadvantages have been recognized by various searchers in this field, as appears from a number of patent publications in which the introduction of the 1α-hydroxy group in the vitamin D compound itself, so after the UV-irradiation, is described. In these Patent Specifications, such as European Patent Application No. 10992 and U.S. Pat. Nos. 4,195,027 and 4,202,829, the 1α-hydroxy group is directly introduced into the vitamin D compound by an allylic oxidation with selenium dioxide or a selenic acid ester. The results of this direct allylic oxidation, however, are not very satisfactory, because the oxidation proves to run off sparingly selectively. In fact, in addition to the desired 1α-hydroxy group, one or more other hydroxy groups are easily introduced into the vitamin D compound.

It has now been found that 1α-hydroxyvitamin D compounds can be prepared in a satisfactory yield and purity by hydroxylating the adduct of a previtamin D compound with a suitable dienophile, in which adduct optionally present hydroxy group(s) is (are) protected, if desired, in the 1α-position and then isolating the 1α-hydroxyvitamin D compound after removing the protecting group or groups.

As examples of suitable dienophiles may be mentioned 1,2,4-triazoline-3,5-diones which are preferably substituted in the 4-position by an alkyl group, a cycloalkyl group or a substituted or non-substituted phenyl group. Other examples of suitable dienophiles are diazaquinones, for example, 3,6-pyridazinedione, 4,5-difluoro-3,6-pyridazinedione and 1,4-phthalazinedione, and other nitrogen-containing dienophiles, for example, dialkylazodicarboxylates.

Dienophiles of the general formula 1, in which A and B are equal or different and represent alkoxy groups having 1 to 4 carbon atoms, or in which A and B together form a phenylimino or o-phenylene group have proved particularly suitable. Preferably used as a starting substance for the preparation of 1α-hydroxyvitamin D compounds is an adduct of a previtamin D compound with a dienophile of the general formula 3, in which A' and B' are equal and represent methoxy groups or ethoxy groups, or in which A' and B' together form a phenylimino or o-phenylene group, that is to say, with 4-phenyl-1,2,4-triazoline-3,5-dione, with dimethyl- or diethylazodicarboxylate or with 1,4-phthalazinedione as a dienophile.

From articles by D. J. Aberhart and A. Chi-Tung Hsu (J. Org. Chem., Vol. 41, No. 12, pp. 2098–2101 (1976)) and W. Reischl and E. Zbiral (Liebigs Ann. Chem. 1978, pp. 745–756) it is known to use 4-phenyl-1,2,4-triazoline-3,5-dione to protect the sensitive triene system in vitamin $D_3$. However, splitting off of the 4-phenyl-1,2,4-triazolidine-3,5-dione-1,2-diyl group yielded a stereo isomer of vitamin $D_3$, namely 5,6-trans-vitamin $D_3$.

It has now been found, however, that introduction of a hydroxy group in the 1α-position in a vitamin or previtamin D compound can be carried out in a satisfactory yield and with a good stereochemical selectivity by starting from the adduct of a previtamin D compound and a suitable dienophile, for example, 4-phenyl-1,2,4-triazoline-3,5-dione, diethylazodicarboxylate or 1,4-phthalazinedione. Moreover, after introduction of the desired hydroxy group, the dienophile group can be easily removed again from said adduct, in which, in contrast with the above-mentioned vitamin $D_3$ adduct, the steric configuration is maintained during the rearrangement to the hydroxylated vitamin D compound.

If one or more hydroxy groups interfering in the hydroxylation reaction should be present in the adduct of the previtamin D compound, said hydroxy group or hydroxy groups can be protected.

The method according to the invention relates in particular to a hydroxylation in the 1α-position starting from an adduct of a previtamin D compound of the general formula 2, in which R is a branched or non-branched, saturated or unsaturated alkyl radical optionally substituted with one or more hydroxy groups or fluorine atoms, and having 7 to 10 carbon atoms, and R' is a hydrogen atom, a hydroxy group, an esterified hydroxy group or an etherified hydroxy group.

Examples of suitable previtamin D compounds are previtamin $D_3$, 25-hydroxyprevitamin $D_3$, 24,25-dihydroxyprevitamin $D_3$ and an esterification product or etherification product of one of these previtamin D compounds with an aliphatic or aromatic carboxylic acid, or with a suitable etherification agent respectively.

Hydroxy groups in the adduct disturbing in the reaction may be protected as described above. These hydroxy groups may be protected before or after the adduct formation, preferably by a reaction with an esterification agent or etherification agent.

Suitable esterification agents are an alkylchlorocarbonate having 2 to 5 carbon atoms, or an aromatic carboxylic acid, a saturated aliphatic carboxylic acid having 1 to 4 carbon atoms, p-toluene sulphonic acid, methane sulphonic acid, trifluoroacetic acid, or a derivative of these acids suitable for the esterification reaction. For the protection of unstable hydroxy groups in the form of an ether, all etherification agents known for this purpose are in principle suitable, for example, a triphenylmethylhalide, 2,3-dihydropyran, or a trialkylsilylhalide or trialkylsilylethoxy methylhalide the alkyl groups of which comprise 1 to 6 carbon atoms. Particularly suitable for this purpose are trimethylsilylchloride, tert.-butyldimethylsilylchloride or trimethylsilyl-ethoxymethylchloride, because these etherification agents readily react with the hydroxy group to be protected to an ether function which on the one hand is sufficiently stable under the reaction circumstances but on the other hand can easily be split with back formation of the original hydroxy group; tert.-butyldimethylsilylchloride is to be preferred because the tert.-butyldimethylsilyl group has proved to be especially suitable as a protective group.

From an article by E. J. Corey and A. Venkateswarlu in J. Am. Chem. Soc. 94 (17), pp. 6190–6191 (1972) it is known to use a tert.-butyldimethylsilyl group to protect a hydroxy group; however, the use of said silyl group for the protection of unstable hydroxy groups in a vitamin D compound or previtamin D compound is not described. The reaction with tert.-butyldimethylsilylchloride can be carried out as described in the above publication by Corey c.s., namely by reacting the chloride and the alcohol with each other in an inert organic solvent, for example, dimethyl formamide, in the presence of an organic base, for example, imidazole, at a temperature between 0° C. and the boiling-point of the solvent, preferably at room temperature.

The 1α-hydroxylation of the adduct of a previtamin D compound as described above can be carried out in various manners, namely by a reaction with a chromium-containing oxidation agent or with selenium dioxide, succeeded by a reduction, or by a reaction with a bromine compound, succeeded by a hydrolysis.

Chromic acid, pyridine dichromate, tert.-butylchromate or a chromiumtrioxide-3,4-dimethylpyrazole complex is to be preferred as a chromium-containing oxidation agent, while the subsequent reduction is preferably carried out with a metal hydride or complex metal hydride. For obtaining the correct steric configuration, the reaction product of lithium aluminium hydride and aluminium chloride is to be preferred as a reduction agent. The oxidation is usually carried out in a polar organic solvent, for example a chlorinated aliphatic hydrocarbon such as dichloromethane, at a temperature between 0° C. and the boiling-point of the solvent used, preferably at room temperature. The reduction with the above reduction agent is preferably carried out in an ether as a solvent, for example, tetrahydrofuran, at a temperature between −100° C. and 0° C., preferably at a temperature between −50° C. and −80° C. The oxidation succeeded by reduction yields the desired 1α-hydroxy adduct compound in a satisfactory stereochemical purity, namely approximately 80%.

Because the reaction of the adduct of a previtamin D compound with a chromium-containing oxidation agent, in which a keto group is to be formed in the 1-position of the previtamin D compound, does not always run off easily, a hydroxylation or a bromination in the 1-position preceding the oxidation is often preferred. This hydroxylation can best be carried out by a reaction with a bromine compound succeeded by a hydrolysis. The resulting mixture of stereoisomers, namely an adduct mixture of 1α- and 1β-hydroxy previtamin D compounds, can be subjected to an oxidation. Besides with the above-mentioned oxidation agents, said oxidation can also be carried out with manganese dioxide. Stereospecific reduction of the resulting ketone yields the desired 1α-hydroxy adduct compound. The brominated previtamin D adduct compound can also directly be subjected to an oxidation reaction. For this oxidation a chromium-containing oxidation agent is best suited, preferably bis(tetrabutylammonium)dichromate or pyridine dichromate. It is not even necessary to isolate this bromo-compound. Immediately following the bromination reaction, the reaction mixture containing the intermediately formed bromo-compound can be subjected to an oxidation reaction. It is also possible of course to isolate the adduct of the 1α-hydroxy-previtamin D compound from the mixture of stereoisomers obtained after hydrolysis, as a result of which the above-mentioned oxidation and reduction may be omitted. However, in order to obtain a good yield of pure 1α-stereoisomer, the by-pass via the 1-keto compound is preferred. N-bromosuccinimide, N,N'-dibromodimethylhydantoin or N-bromophthalimide are preferably used as bromine compounds for the above-mentioned bromination, while the hydrolysis is usually carried out subsequently with a mixture of water and a water-miscible organic solvent. The bromination reaction is preferably carried out in a halide-containing organic solvent, for example, a chlorinated aliphatic hydrocarbon, for example, carbon tetrachloride, or in an aliphatic hydrocarbon, for example, n-hexane or in mixtures of said solvents, in the presence of an acid scavenger, for example, an organic base, for example S-collidine, and under irradiation or in the presence of a catalytic amount of a compound initiating a radical reaction, for example, a peroxide or an azo compound, for example, α,α'-azoisobutyronitrile, at a reaction temperature between room temperature and the boiling-point of the solvent used, preferably at the boiling-point of the solvent. After distilling off the solvent, the resulting 1-bromine compound is subsequently hydrolysed with a mixture of water and a water-miscible organic solvent, for example, dioxane or acetone. Said hydrolysis can be carried out in the presence of silver ions, for example, in the form of silver carbonate on celite as a carrier, or with moist silicon dioxide.

The removal of the protective group or groups of the 1α-hydroxylated adduct may take place in a manner which is known per se for the removal of these groups. For example, the protective tert.-butyldimethylsilyl group can be removed as described in the above-mentioned article by Corey c.s., namely by a reaction with a fluorine compound, for example, tetrabutylammoniumfluoride, in an inert organic solvent, for example, an ether such as tetrahydrofuran. Splitting off with an acid, if desired adsorbed on a carrier, for example silicon dioxide, is also possible. The protective dienophile group can simply be removed as described for the 4-phenyl-1,2,4-triazolidine-3,5-dione-1,2-diyl group in the above-mentioned article by Reischl c.s., namely by reaction with a base in a protic or aprotic polar solvent or a mixture thereof, preferably with an alkali metal hydroxide in an alcohol, for example, methanol or n-butanol, at a temperature between 0° C. and the boiling-point of the alcohol used, preferably at the boiling-point of the alcohol, and if desired in the presence of one or more oxidation agents. The splitting off can also be carried out by means of an alkali metal hydride, for example, lithium aluminium hydride, in an inert aprotic solvent, with a sodium alcoholate in an alcohol, or with S-collidine.

The removal of the protective dienophile group can be carried out at each suitable instant, e.g. after the introduction of the hydroxy group into the 1-position. In that case the mixture of stereoisomers has to be converted to the pure 1α-hydroxyvitamin D compound, preferably as follows: Removal of both protective groups, viz. the dienophile group and e.g. the silylether group, from the before-mentioned mixture of stereoisomers obtained after hydrolysis yields a mixture of 1α- and 1β-hydroxyvitamin D compounds. Oxidation of this mixture, preferably with manganese dioxide, leads to the corresponding 1-oxo-vitamin D compound, which can be reduced stereospecifically to the desired 1α-hydroxyvitamin D compound as mentioned before for the preparation of the 1α-hydroxy adduct compound.

1α-Hydroxy-previtamin D compounds are new. The present invention therefore also relates to 1α-hydroxy-previtamin D compounds and particularly to 1α-hydroxy-previtamin D compounds of the general formula 2b, wherein R and R' have the above-given meanings, for example 1α-hydroxy-previtamin $D_3$, 1α,25-dihydroxy-previtamin $D_3$ and 1α,24,25-trihydroxy-previtamin $D_3$.

The adduct of a previtamin D compound with a sutiable dienophile to be used for the above-described 1α-hydroxylation reaction is new.

The present invention therefore also relates to the adduct of a previtamin D compound with a dienophile of the general formula 3, in which A' and B' are equal and represent methoxy groups or ethoxy groups, or in which A' and B' together constitute a phenylimino or o-phenylene group, and in particular to an adduct of said dienophile with a previtamin D compound of the general formula 2, in which R and R' have the above-given meanings, for example the following compounds: previtamin $D_3$, 25-hydroxyprevitamin $D_3$, 24,25-dihydroxyprevitamin $D_3$ and an esterification product or etherification product of one of these previtamin D compounds with a aliphatic or aromatic carboxylic acid or with a suitable etherification agent respectively.

The present invention further relates to an adduct of a tachysterol compound, in particular a compound of the general formula 2a, wherein R and R' have the above-given meanings, e.g. tachysterol, with a dienophile of the general formula 3, wherein A' and B' have the above meanings. In principle this adduct can also be used for the preparation of 1α-hydroxylated vitamin D or previtamin D compounds.

Previtamin D compounds are known in the literature. As early as 1949, Velluz and collaborators (Bull. Soc. Ch. Fr. 1949, 501) discovered previtamin $D_3$, while in 1955 Koevoet c.s. (Recueil 74 (1955), 788–792) devoted an article to this compound. From these papers it appears that previtamin $D_3$ can be obtained from vitamin $D_3$ by equilibration, but as a result of energetically unfavourable structural changes, can convert again very easily into the starting substance at a small rise in temperature. Moreover, previtamin $D_3$ is not crystalline and can hence substantially not be obtained in a pure form. This instability and difficult handlability is probably the reason why so far little attention has been paid in the literature to previtamin D compounds for synthetic purposes. Essentially the same applies to a stereo-isomer of previtamin $D_3$, viz. tachysterol, which is also discussed by Koevoet et al. in Recueil 74, 1955, 788–792. The above-mentioned U.S. Pat. No. 4,202,829 does mention a previtamin D compound as a starting substance for the allylic oxidation with selenium oxide, in which the desired 1-hydroxylated vitamin D compound can be obtained after thermal isomerisation. However, the impression is not gained that a previtamin D compound would be preferred to other stereoisomers mentioned as starting substances in said Patent Specification, for example a vitamin D compound of a 3,6-trans-vitamin D compound, so that the same poor stereoselectivity may be expected. It is therefore surprising that reaction of an unstable previtamin D or tachysterol compound, for example, of previtamin D or tachysterol or of a derivative of one of these compounds with a suitable dienophile, for example, 4-phenyl-1,2,4-triazoline-3,5-dione, diethyl azodicarboxylate or 1,4-phthalazinedione, yields such a stable adduct that a purification by means of a recrystallization can be carried out without any objections.

An adduct of a previtamin D or tachysterol compound and a dienophile of the general formula 3, in which A' and B' have the above meanings, can be prepared in a manner known per se for the preparation of related compounds. For example, the adduct can be prepared in a manner as is known for the preparation of the adduct of a vitamin D compound and 4-phenyl-1,2,4-triazoline-3,5-dione, for example as described in the above-mentioned articles by Aberhart c.s. and by Reischl. For that purpose, the previtamin D or tachysterol compound is reacted with the dienophile in an inert organic solvent, for example, an ester, for example, ethyl acetate, a chlorinated aliphatic hydrocarbon, for example, dichloromethane, an aromatic hydrocarbon, for example, toluene, an ether, for example, tetrahydrofuran, a ketone, for example, acetone, or mixtures of these solvents, at room temperature or a slightly reduced temperature, preferably at approximately 0° C.

As a previtamin D or tachysterol compound is preferably chosen a compound of the general formula 2 or 2a, in which R and R' have the above-given meanings, such as previtamin $D_3$, 25-hydroxy-previtamin $D_3$, 24,25-dihydroxyprevitamin $D_3$, tachysterol, or an esterification product or etherification product of one of those compounds with an aliphatic or aromatic carboxylic acid or with a suitable etherification agent respectively.

It has been found that the adduct of a previtamin D compound and a dienophile of the general formula 3 can also be prepared in a different manner, namely by subjecting the corresponding 7-dehydrocholesterol compound to UV-irradiation in a suitable organic solvent, and, after recovery of the non-converted starting material, reacting the irradiation product with the dienophile. As a 7-dehydrocholesterol compound is preferably used a compound of the general formula 4, in which R and R' have the above-given meanings, for example, 7-dehydrocholesterol, 25-hydroxy-7-dehydrocholesterol, 24,25-dihydroxy-7-dehydrocholesterol, or an ester or ether thereof. The UV-irradiation is carried out in an inert organic solvent, preferably an ether, such as tetrahydrofuran, or diethyl ether, at room temperature or a slightly reduced temperature. After the irradiation, the non-converted starting material can be recovered, for example, by crystallization from a suitable solvent succeeded by filtration. The subsequent reaction with the dienophile of the general formula 3 is preferably carried out at approximately the same temperature in a solution of an inert organic solvent, preferably a chlorinated aliphatic hydrocarbon, such as dichloromethane.

The present invention will now be described in greater detail with reference to the following specific examples.

EXAMPLE I

Preparation of the adduct of previtamin $D_3$-butyrate and 4-phenyl-1,2,4-triazoline-3,5-dione.

(a) 9.54 g Of dicyclohexyl carbodiimide were added under nitrogen at 0° C. to a solution of 17.77 g of vitamin $D_3$ (formula 5, R=1,5-dimethyl hexyl), 4.03 g of butyric acid and 0.656 g of dimethylamino pyridine in 90 ml of dry dichloromethane cooled to approximately 0° C. After stirring for 10 minutes at 0° C. the reaction mixture was allowed to reach room temperature. The esterifification reaction was followed by thin-layer chromatography (eluent: iso-octane/ethyl acetate=95/5). After 3 to 4 hours, the resulting suspension was filtered off, after which the precipitate was washed with dichloromethane. Filtrate and washing liquid were combined and washed successively with 0.1N hydrochloric acid and a saturated NaCl solution. The organic phase was dried on magnesium sulphate. After concentration under reduced pressure, the residue was dissolved in a small amount of acetone, after which the solution was cooled to a temperature between 0° C. and −20° C.; the desired butyrate crystallized (formula 6). The product was filtered off; yield 18.354 g; melting-point 60° C.

(b) A quantity of 23.11 g of vitamin $D_3$-butyrate (formula 6) was melted in a round-bottomed flask on an oil bath. The substantially bright light-yellow melt was kept at a temperature of 110° to 120° C. for 45 minutes. After cooling to 70° C., 99 ml of cold acetone were added to the melt. The resulting solution was then cooled further to 8° C. and seeded with a few crystals of vitamin $D_3$-butyrate. After leaving to stand the reaction mixture at −20° C. for 12 hours, the crystalline materials was filtered off; it consisted of 11.7 g of non-converted vitamin $D_3$-butyrate. The mother liquor was evaporated under reduced pressure at a temperature of at most 20° C. The residue, a light-yellow resin, weighed 10.9 g and consisted of a mixture of vitamin $D_3$-butyrate and previtamin $D_3$-butyrate (formulae 6 and 7); identification was by means of thin-layer chromatography.

(c) A solution of 7.25 g of 4-phenyl-1,2,4-trizoline-3,5-dione in 90 ml of dry dichloromethane was added dropwise under nitrogen and while stirring at 0° C. to a solution of 18.8 g of a mixture of vitamin $D_3$-butyrate and previtamin $D_3$-butyrate (formulae 6 and 7) in 330 ml of dry dichloromethane. The solution which at the end of the reaction had a light red colour, was concentrated under reduced pressure, after which the oily residue was dissolved in a small amount of acetone. The desired adduct of previtamin $D_3$-butyrate and 4-phenyl-1,2,4-triazoline-3,5-dione (formula 8) crystallized at −10° C. and was filtered off and then washed with cold hexane. Concentration of the filtrate yielded a second quantity of crystalline adduct. The collected crystalline material was recrystallized from acetone and washed with cold hexane; yield 14.87 g. Physical-chemical characteristics: UV: $\lambda_{max}$=218 nm; $R_f$ (ethyl acetate/isooctane: 3/7)=0.34; melting-point 153° C. The configuration shown in formula 8 was determined by means of X-ray diffraction analysis.

EXAMPLE II (a) Preparation of the adduct of previtamin $D_3$ and 4-phenyl-1,2,4-triazoline-3,5-dione.

A solution of 106.0 g of 7-dehydrocholesterol (formula 4, R=1,5-dimethylhexyl) in 2 l of tetrahydrofuran purified by distillation was irradiated for 25 minutes in a nitrogen atmosphere at a temperature between 10° and 15° C. The irradiation was carried out in an apparatus in which the liquid to be irradiated was circulated by pumping and in which a 1500 W high-pressure mercury lamp was placed. The solution obtained after irradiation was evaporated under reduced pressure at a temperature of at most 20° C. The solid residue was stirred two times with 300 ml of methanol under nitrogen. The insoluble non-converted 7-dehydrocholesterol was filtered off (86.5 g) and the filtrate was concentrated to a volume of 50 ml at a temperature of at most 20° C. Another 1.0 g of non-converted starting material was recovered by cooling to −20° C. The filtrate was evaporated to a foamy product which was dried in a high vacuum; weight 19.0 g.

To a solution of this residue in 300 ml of dichloromethane was added dropwise at 10° C. a solution of 8.6 g of 4-phenyl-1,2,4-triazoline-3,5-dione in 100 ml of dichloromethane. Of the resulting reaction mixture the solvent was distilled off under reduced pressure, after which the residue was dissolved in 60 ml of acetone. By cooling the solution to −20° C., the desired adduct (formula 9) crystallized in a yield of 6.9 g; melting-point 152°-153° C. The mother liquor, after evaporation, was chromatographed over 300 g of $SiO_2$ (Merck) and eluated with a mixture of toluene and acetone (gradient elution). In this manner another 6.7 g of the desired adduct was obtained. Total yield 13.6 g.

(b) In a corresponding manner the adduct of 25-hydroxy-previtamin $D_3$ and 4-phenyl-1,2,4-triazoline-3,5-dione was prepared from 7-dehydro-25-hydroxycholesterol. The product was identified by means of its NMR spectrum.

EXAMPLE III

Preparation of 1α-hydroxyvitamin $D_3$.

(a) A solution of 13.675 g of the adduct (formula 8) in 200 ml of dry methanol, in which 12 g of potassium carbonate had been suspended, was refluxed for 45 minutes. The resulting suspension was concentrated under reduced pressure, after which the residue was taken up in a mixture of water and diethyl ether. The ether phase was separated and washed successively with dilute sulphuric acid (14 ml of concentrated sulphuric acid in 100 ml of water), a sodium carbonate solution and a saturated NaCl solution. After drying on magnesium sulphate, the solvent of the organic phase was distilled off. The residue was recrystallized from a small amount of acetone, 10.86 g of the desired alcohol being obtained (formula 9); melting-point 153°-153.5° C.

(b) A solution of 11.79 g of the alcohol (formula 9), 3.587 g of imidazole and 4.450 g of tert.-butyl dimethyl silylchloride in 200 ml of dimethyl formamide was stirred under nitrogen at room temperature for 45 minutes. After 15 minutes a white-crystalline precipitate was formed. After 45 minutes, hexane was added until two bright phases had formed. The dimethyl formamide phase was extracted with hexane; the collected hexane phases were washed successively with 0.1N hydrochloric acid, water, a sodium bicarbonate solution and a saturated NaCl solution, and then dried on magnesium sulphate. After concentration under reduced pressure, the oily residue was dissolved in 200 ml of boiling acetonitrile. Upon cooling, the desired silyl ether (formula 10) crystallized in a yield of 13.47 g; melting-point 137° C. Change in $^1$H NMR spectrum in comparison with the spectrum of the butyrate of formula 8: the signal at $\delta=4.93$ had shifted to $\delta=3.78$ (1H, m, C$_3$-H).

Essentially in the same way as described in Example III (b), the trimethylsilyl ether of the adduct of previtamin D$_3$ and 4-phenyl-1,2,4-triazoline-3,5-dione was prepared in a yield of 75%; melting-point 165°-167° C.; UV (CH$_3$OH): $\lambda_{max}=217$ nm; R$_f$ (hexane/acetone: 8/2)=0.40.

(c) 592 mg Of N-bromosuccinimide and a crystal of $\alpha,\alpha'$-azoisobutyronitrile were added to a solution of 1.50 g of silyl ether (formula 10) in 20 ml of dry carbon tetrachloride. The solution was heated to 110°-120° C. under nitrogen in 5 to 10 minutes. The solution was then cooled again in an ice bath and then filtered over celite. The solvent was distilled off under reduced pressure, after which the residue was dissolved in 15 ml of acetone. 0.3 ml of water was slowly added dropwise to this solution and 1.3 g of silver carbonate on celite was then added portion-wise, the reaction mixture was shielded from the light. The reaction was followed with thin-layer chromatography (eluent: benzene/acetone=9/1). After 10 hours the reaction mixture was filtered over celite, after which the solvent was distilled off under reduced pressure. The residue was taken up in diethyl ether, washed with a saturated NaCl solution and dried on magnesium sulphate. After concentration under reduced pressure and purification by column chromatography with benzene/ethyl acetate 80/20 v/v as an eluent, a total of 783 mg of product were obtained consisting of 502 mg of a mixture of the alcohols of formulae 11 and 12, 126 mg of alcohol of formula 11 and 155 mg of alcohol of formula 12. The weight ratio of alcohols of formulae 11 and 12 in the total reaction product is 3:7; this was determined by means of NMR spectroscopy.

R$_f$ value of alcohol of formula 11: R$_f$ (benzene/ethyl acetate=8/2):0.39;

R$_f$ (benzene/ethyl acetate=9/1):0.38.

Ditto of alcohol of formula 12: R$_f$ (benzene/ethyl acetate=8/2):0.33;

R$_f$ (benzene/ethyl acetate=9/1):0.30.

(d) A solution of 931 mg of the alcohol mixture of formulae 11 and 12 in 1.5 ml of dry methylene chloride was added to a solution of 1.015 g of pyridine dichromate in 2.5 ml of dry methylene chloride. After leaving to stand at room temperature for 10 hours, approximately 10 ml of diethyl ether were added. The resulting suspension was filtered, after which the precipitate was washed with ether. Of the collected ether fractions the solvent was distilled off under reduced pressure, after which the residue was purified by column chromatography using a mixture of isooctane and ethyl acetate as an eluent in a volume ratio of 9:1. The desired silyl ether-enone (formula 13) was obtained in a yield of 702 mg; melting-point 97°-98° C. The signals of the enone system in the $^{13}$C NMR-spectrum are at 131.1, 149.5 and 195.0 ppm.

UV: $\lambda_{max}=222$ nm; shoulder at 240 nm.

(e) The silyl-ether enone of formula 13 could also be prepared from the silyl ether of formula 10 by a direct oxidation of the intermediately formed bromo-compound but without isolating this bromide.

To a boiling solution of 1.0 g of the silyl ether of formula 10, obtained as described in Example III (a), in 16 ml of dry hexane are added successively 0.196 ml of collidine, a catalytic amount of bis(4-tert.-butylcyclohexyl)peroxidicarbonate and 425 mg of dimethyldibromohydantoin. After 20 minutes the suspension is filtered over celite and washed with dry hexane. The filtrate is concentrated under reduced pressure and dissolved in 10 ml of dry chloroform.

Bis(tetrabutylammonium)dichromate in an amount of 5.8 g is added to the above solution; the reaction mixture is refluxed for 2 hours. After cooling down to room temperature the suspension is filtered over silicagel and washed with 250 ml of diethylether. The combined filtrate and washing liquid are concentrated under reduced pressure. The residue is purified by column-chromatography; eluent:hexane/acetone=95/5. The compound obtained is identical with the compound prepared as described in Example III (d): formula 13.

In the same way the trimethylsilyl ether of the above adduct could be converted into the corresponding silyl-ether enone. The trimethylsilyl ether-enone obtained is dissolved in tetrahydrofuran and without further purification directly converted into the desired alcohol-enone of formula 14 (see Example III (e) for physical characteristics) by a treatment with a diluted (1.5M) hydrochloric acid solution.

(f) The tert.-butyl dimethylsilyl ether-enone of formula 13 could also be prepared as follows.

The 1-bromosubstituted compound was prepared by a bromination reaction of the silyl ether of formula 10 exactly as described in Example III (c). After the bromination 10 g of the residue was dissolved in 60 ml of dichloromethane. To this solution 10 g of pyridine dichromate was added, after which the reaction mixture was stirred at room temperature for 18 hours. After dilution with 500 ml of diethylether the reaction mixture was filtered off. The filtrate was concentrated under reduced pressure and yielded 3.5 g of a compound which was identical with the compound of formula 13, prepared according to Example III (d).

(g) 10.2 Ml of a 1 molar solution of tetrabutylammoniumfluoride in tetrahydrofuran were added dropwise under nitrogen at $-10°$ C. to a solution of 700 mg of the enone of formula 13 and 0.47 ml of butyric acid in 10 ml of dry tetrahydrofuran. After stirring for 3 hours at room temperature, the reaction mixture was diluted with approximately 10 ml of diethyl ether and washed successively with a saturated bicarbonate solution and a saturated NaCl solution. The organic phase was then dried on magnesium sulphate and concentrated under reduced pressure. The residue was purified by column chromatography using a mixture of benzene and acetone as an eluent in a volume ratio of 9:1. The desired alcohol-enone (formula 14) was obtained in a yield of 528 mg; melting-point 101°-102° C.

(h) A solution of 308 mg of aluminium chloride in 3.86 ml of dry tetrahydrofuran was added dropwise with vigorous stirring to a suspension of 263 mg of lithium aluminium hydride in 20 ml of dry tetrahydrofuran at room temperature. 428 Mg of the alcohol enone of formula 14 in 3 ml of dry tetrahydrofuran were added dropwise to this suspension at −70° C. After stirring for 1 hour at −60° C., approximately 2 ml of diethyl ether were added and then 5% hydrochloric acid. After allowing the reaction mixture to reach room temperature, the organic phase was separated and washed successively with 5% hydrochloric acid, a saturated bicarbonate solution and a saturated NaCl solution. After drying on magnesium sulphate the solution was concentrated under reduced pressure and was then purified by column chromatography using a mixture of benzene and acetone as an eluent in a volume ratio of 8:2. The desired diol (formula 15) was obtained in a yield of 421 mg; melting-point 165°–167° C. (diethyl ether).

$R_f$(benzene/acetone=7/3):0.25.

(i) A crude residue of the diol of formula 15 obtained from 10 mg of the alcohol-enone (formula 14) according to the method described in Example III (h) but without the column chromatographic purification, was dissolved in 2 ml of a 3% solution (weight/volume) of potassium hydroxide in n-butanol; this solution was refluxed for 2 hours. After diluting with approximately 5 ml of diethyl ether the solution was washed with 5% hydrochloric acid until acid reaction, then washed neutral with a saturated NaCl solution and finally dried on magnesium sulphate. After distilling off the solvent under reduced pressure, the final product was purified by means of Multiple-TLC-chromatography using a mixture of hexane and acetone as an eluent in a volume ratio of 8:2. 3 Mg of an alcohol mixture of formulae 16 and 17 were obtained in a weight ratio of 8:2. The alcohol of formula 16 is 1α-hydroxyvitamin $D_3$.

In a corresponding manner, 32 mg of pure 1α-hydroxyvitamin $D_3$ of formula 16 were obtained from 100 mg of the diol of formula 15 obtained according to Example III (h) after purification by chromatography and recrystallization. Physical-chemical characteristics: melting-point 134° C. (after recrystallization from n-hexane); UV: $\lambda_{max}$ ($CH_3OH$)=265 nm; $\lambda_{min}$ ($CH_3OH$)=228 nm.

(j) The reaction described in Example III (i) can also be carried out as follows:

150 Mg of the purified diol of formula 15 obtained according to Example III (h) were dissolved in 5 ml of methanol. After heating the solution to boiling, 2 ml of 15N aqueous potassium hydroxide were added, after which the mixture was refluxed for 24 hours. The reaction mixture was then processed in the same manner as described in Example III (i), 60 mg of pure 1α-hydroxyvitamin $D_3$ of formula 16 being obtained; the product was identical to the above pure substance obtained according to Example III (i).

EXAMPLE IV

Preparation of 1α-hydroxyvitamin $R_3$.

(a) The alcohol of formula 11 was prepared as described in Example III (a)–(c).

A solution of 36 mg of the alcohol of formula 11 in 5 ml of a solution of 3% potassium hydroxide in n-butanol (weight/volume) was heated for 2 hours at 110° C. The solution was then diluted with approximately 10 ml of diethyl ether and washed with 5% hydrochloric acid until acid reaction. The solution was then washed neutral with a saturated NaCl solution and dried on magnesium sulphate. After distilling off the solvent under reduced pressure, the residue was taken up in diethyl ether, after which the solution was again evaporated to dryness.

(b) The residue containing the alcohol-silyl ethers of formulae 18 and 19 was dissolved in 2 ml of dry tetrahydrofuran. 141 Mg of tetrabutylammoniumfluoride were added to this solution, after which the reaction mixture was stirred for 20 hours at room temperature while shielded from the light. After dilution with approximately 4 ml of diethyl ether, the solution was washed successively with water and a saturated NaCl solution. The organic phase was then dried on magnesium sulphate and concentrated under reduced pressure. The residue was dissolved in benzene and refluxed for 2 hours. After distilling off the solvent, the residue was purified by column chromatography using a mixture of hexane and acetone as an eluent in a volume ratio of 8:2. 6 Mg of 1α-hydroxyvitamin $D_3$ were obtained; the product was identical to the pure substance obtained according to Example III (i).

EXAMPLE V

Preparation of the adduct of previtamin $D_3$-butyrate and diethyl azodicarboxylate.

3.85 g (4.8 ml) of diethyl azodicarboxylate were added dropwise at room temperature under nitrogen and with stirring to a solution of 13.7 g of a mixture of vitamin $D_3$-butyrate and previtamin $D_3$-butyrate (formulae 6 and 7), obtained according to Example I (a)–(b), in 65 ml of dry methylene chloride. The reaction mixture was stirred for 24 hours in which the reaction was followed with thin-layer chromatography; eluent: hexane/acetone=8/2 v/v. The solvent was then distilled off under reduced pressure. the resulting material was purified by means of column chromatography (HPLC) using a mixture of hexane in ethyl acetate as an eluent in a volumne ratio of 9:1. The desired adduct of formula 20 was isolated in a yield of 10.1 g; $R_f$(hexane/acetone: 8/2)=0.51.

The structure was established by means of NMR-spectroscopy.

EXAMPLE VI

Preparation of the adduct of previtamin $D_3$-butyrate and 1.4-phthalazinedione.

A solution of 5.432 g of lead tetraacetate in 40 ml of dry dichloromethane and 2 ml of acetic acid is added dropwise under nitrogen and while stirring at 0° C. to a suspension of 4.967 g of 1.4-phthalazinedione in a solution of 4.64 g of a mixture of vitamin $D_3$-butyrate and previtamin $D_3$-butyrate in 60 ml of dry dichloromethane. After stirring for 4 hours at room temperature the suspension is filtered off and washed with diethyl ether and dichloromethane successively. The combined organic phase is washed successively with a saturated NaCl solution, 5% hydrochloric acid, a saturated NaCl solution, a saturated $NaHCO_3$ solution and a saturated NaCl solution. After drying on magnesium sulphate and concentration under reduced pressure the residue obtained is purified by column-chromatography (eluent: hexane/ethylacetate:85/15). The desired adduct of formula 27 is isolated in a yield of 3.2025 g; UV ($CH_3OH$): $\lambda_{max}$=216 nm; $R_f$ (hexane/acetone:8/2)=0.35. The structure is established by means of NMR analysis.

EXAMPLE VII

Preparation of the adduct of tachysterol 3,5-dinitro-4-methylbenzoate and 4-phenyl-1,2,4-triazoline-3,5-dione.

A solution of 0.3767 mmol of 4-phenyl-1,2,4-triazoline-3,5-dione in 1 ml of ethylacetate is added dropwise at 0° C. under nitrogen to a solution of 223 mg (0.3767 mmol) of tachysterol 3.5-dinitro-4-methylbenzoate of formula 28 (R=1,5-dimethylhexyl) in 2 ml of dry dichloromethane. After stirring for 15 minutes at room temperature the solution is concentrated under reduced pressure. The residue is purified by column-chromatography (eluent:hexane/acetone: 9/1) and yielded 247 mg of the desired adduct of formula 29. The structure was established by means of its NMR-spectrum. UV (CH$_3$OH): $\lambda_{max}$=219 nm; oil; R$_f$ (hexane/acetone:8/2)=0.19.

EXAMPLE VIII

Preparation of 1α-hydroxyvitamin D$_3$.

(a) A solution of 9.1 g of the adduct of formula 20 obtained according to Example V in 100 ml of dry methanol, in which 2 g of potassium carbonate had been suspended, was stirred under nitrogen at room temperature for approximately 4 hours. The reaction was followed with thin-layer chromatography; eluent: hexane/acetone=8/2 v/v. After filtering and washing the precipitate with methanol, the solvent of the solution was distilled off under reduced pressure. The residue was taken up in diethyl ether and washed successively with water and a saturated NaCl solution until neutral. After drying on magnesium sulphate the solvent of the organic phase was distilled off. The desired alcohol of formula 21 was obtained in a yield of 7.4 g; R$_f$(hexane-/acetone: 8/2)=0.25.

In the same way, the adduct of previtamin D$_3$ and 1.4-phthalazinedione is prepared from the adduct obtained as described in Example VI: UV (CH$_3$OH): $\lambda_{max}$=216 nm; R$_f$(hexane/acetone:7/3)=0.48.

Also in the same way, the adduct of tachysterol and 4-phenyl-1,2,4-triazoline-3,5-dione is prepared from the adduct according to Example VII: UV (CH$_3$OH): $\lambda_{max}$=211 nm; R$_f$(hexane/acetone:8/2)=0.16.

The above adducts were identified by means of their NMR spectra.

(b) A solution of 4.0 g of the alcohol of formula 21, 1.2 g of imidazole and 1.5 g of tert.-butyl dimethylsilyl chloride in 60 ml of dimethyl formamide was stirred under nitrogen at room temperature for approximately 45 minutes. The reaction was again followed with thin-layer chromatography; eluent: hexane/acetone 8/2 v/v. An equal volume of hexane was then added and the same quantity of saturated NaCl solution. After stirring for approximately 10 minutes, the hexane layer was separated and the dimethyl formamide layer was extracted once again with the same quantity of hexane. The collected hexane phases were washed successively with water and a saturated NaCl solution and then dried on magnesium sulphate. After filtering and concentrating, the resinous residue was purified by column chromatography (HPLC) using a mixture of hexane and ethyl acetate as an eluent in a volume ratio of 9:1, after which the desired silyl ether (formula 22) was obtained in a yield of 4.0 g; R$_f$(hexane/acetone:8/2)=0.54. The product was identified by means of NMR-spectroscopy.

In the same way, the tert.-butyldimethylsilylether of the adduct of previtamin D$_3$ and 1.4-phthalazinedione is prepared: R$_f$ (hexane/acetone:8/2)=0.49; UV (CH$_3$OH): $\lambda_{max}$=218 nm.

Also in the same way, the tert.-butyldimethylsilyl ether of the adduct of tachysterol and 4-phenyl-1,2,4-triazoline-3,5-dione is prepared: R$_f$ (hexane/acetone:8/2)=0.60; UV (CH$_3$OH): $\lambda_{max}$=211 nm.

(c) 286 Mg of dimethyl pyrazole were added at once to a suspension of 298 mg of CrO$_3$ in 2.5 ml of dry methylene chlororide at −20° C. After stirring at −20° C. for 20 minutes, a solution of 100 mg of the above-described silyl ether of formula 22 in 1 ml of dry methylene chloride was added. The suspension was stirred for ample time at a temperature between −10° and −20° C., while the course of the reaction was followed with thin-layer chromatography using hexane/acetone as an eluent in a volume ratio 8/2. After termination of the reaction, 2 ml of 5N aqueous sodium hydroxide were added, after which the mixture was stirred at 0° C. for 1 hour. The organic layer was washed successively with 5% hydrochloric acid, water and a saturated NaCl solution. After drying on magnesium sulphate and concentrating under reduced pressure, the residue was purified by means of column chromatography using a mixture of hexane and acetone as an eluent in a volume ratio of 96:4. The desired silylether-enone of formula 23 was obtained in a yield of 35 mg. The product is an oil and was characterized by UV-absorption spectrum and NMR-spectrum:

UV: $\lambda_{max}$ (CH$_3$OH)=246 nm; R$_f$ (hexane/acetone:8/2)=0.38. The NMR spectrum was in agreement with the desired structure.

In the same way the silylether-enone of the adduct of previtamin D$_3$ and 1.4-phthalazinedione is prepared: R$_f$ (hexane/acetone:7/3)=0.33; UV (CH$_3$OH): $\lambda_{max}$=217 nm, 242 nm.

The same silylether-enone could be prepared by the method exactly as described in Example III (e).

By the same method as described in Example III (e), the silylether-enone of the adduct of tachysterol and 4-phenyl-1,2,4-triazoline-3,5-dione could be prepared.

(d) 1.75 ml of a 1 molar solution of tetrabutylammoniumfluoride and tetrahydrofuran were added dropwise at room temperature and under nitrogen to a solution of 120 mg of the enone of formula 23 and 0.0853 ml of butyric acid in 2 ml of dry tetrahydrofuran. After stirring for 5 hours at room temperature, the reaction mixture was diluted with approximately 10 ml of diethyl ether and washed successively with a saturated bicarbonate solution and a saturated NaCl solution. The organic phase was then dried on magnesium sulphate and concentrated under reduced pressure. The residue was purified by means of column chromatography using a mixture of hexane and acetone as an eluent in a volume ratio of 9:1. The desired alcohol-enone of formula 24 was obtained in a yield of 72 mg. The product is an oil and was characterized by the IR-absorption spectrum. UV (CH$_3$OH): $\lambda_{max}$=306 nm, 246 nm.

In the same way, the alcohol-enone of the adduct of previtamin D$_3$ and 1.4-phthalazinedione is prepared; R$_f$ (hexane/acetone:7/3)=0.19; UV(CH$_3$OH): $\lambda_{max}$=217 nm, 242 nm.

(e) A solution of 40.9 mg of aluminium chloride in 0.452 ml of dry tetrahydrofuran was added dropwise to a suspension of 34.9 mg of lithium aluminium hydride in 2.6 ml of dry tetrahydrofuran at room temperature. While stirring vigorously, a solution of 70 mg of the alcohol-enone of formula 24 in 0.4 ml of dry tetrahydrofuran was added dropwise to this suspension at −70° C. After stirring at −60° C. for 1 hour, 2 ml of diethyl ether were added, succeeded by 2 ml of 5% hydrochloric acid. The ether layer was separated at room temperature and washed successively with 5% hydrochloric acid, a saturated sodium bicarbonate solution and a saturated NaCl solution. After drying on magnesium sulphate, the solution was concentrated under reduced pressure, after which the resulting product was purified by means of column chromatography using hexane-/acetone (8/2 v/v) as an eluent. The alcohols of formulae 25 and 26 were obtained in a yield of 44 mg, in a weight ratio of 65 and 35%, respectively.

Alcohol of formula 25: $R_f$ (hexane/acetone=7/3 v/v):0.34;

Alcohol of formula 26: $R_f$ (hexane/acetone=7/3 v)v):0.43.

In the same way, a mixture of diols of the adduct of previtamin $D_3$ and 1.4-phthaloazinedione is prepared, wherein the α-hydroxyisomer is mainly present: $R_f$ (hexane/acetone: 6/4)=0.18.

(f) A solution of 40 mg of the alcohols of formulae 25 and 26 in 1.5 ml of methanol was stirred at 80°–85° C. 1.5 ml of 15N aqueous potassium hydroxide was slowly added dropwise. The reaction mixture was then shielded from the light and stirred for 12 hours. The reaction mixture was then poured in a six-fold excess of a mixture of diethyl ether and a saturated NaCl solution, after which the aqueous layer was extracted another three times with diethyl ether. The collected ethereal phases were washed successively with 5% hydrochloric acid, a saturated sodium bicarbonate solution and a saturated NaCl solution. After drying on magnesium sulphate, the solution was concentrated under reduced pressure, after which the residue was purified by means of column chromatography; eluent: hexane/acetone=85/15 v/v. 6.5 mg of a mixture of 1α-hydroxyvitamin $D_3$ and 1β-hydroxyvitamin $D_3$ of formulae 16 and 17, respectively, were obtained, in which mixture the 1α-isomer was mainly present. The 1α-hydroxyvitamin $D_3$ is obtained in a yield of 51.3%. The mixture also contained a small amount of 1α-hydroxy-previtamin $D_3$ in a yield of 9.2% (HPLC).

In the same way, the mixture of diols of the adduct of previtamin $D_3$ and 1.4-phthalazinedione is converted to 1-hydroxyvitamin $D_3$: 35% of 1α-hydroxyvitamin $D_3$ and 4% of 1α-hydroxy-previtamin $D_3$.

EXAMPLE IX

Preparation of 1α-hydroxyvitamin $D_3$.

The mixture of 1α- and 1β-hydroxyvitamin $D_3$, prepared according to Example IV (a) and (b) could be easily converted to pure 1α-hydroxyvitamin $D_3$ by an oxidation reaction succeeded by a stereospecific reduction as follows.

(a) The mixture of hydroxylated vitamin $D_3$ in an amount of 100 mg is added to a suspension of 653 mg of freshly prepared $MnO_2$ in dry dichloromethane under an argon blanket. The mixture is stirred at 40° C., while after 12 and 24 hours additional 325 mg amounts of fresh $MnO_2$ are added. After 48 hours the suspension is filtered over celite, washed with 100 ml of dry dichloromethane and concentrated under reduced pressure. The residue is purified by HPLC (hexane/acetone:85/15) and yielded 18 mg of the 1-keto compound; UV ($CH_3OH$): $\lambda_{max}=210$ nm, 245 nm.

(b) The stereospecific reduction of the ketocompound is carried out exactly as described in Example III (h). After a purification by means of HPLC (benzene/acetone:8/2) 1α-hydroxyvitamin $D_3$ is obtained in a yield of 28%. According to 360 MHz $^1$H-NMR the product has a stereospecificity of 1α-hydroxyvitamin $D_3$ above 95%.

EXAMPLE X

Preparation of 1α-hydroxy-previtamin $D_3$.

The purified diol of formula 15, obtained as described in Example III (h), in an amount of 500 mg is dissolved in 25 ml of methanol. After addition of 25 ml of 15N aqueous KOH the reaction mixture is heated in an oil bath on 110° C. Then the reaction mixture is poured on a mixture of ice and water and extracted with diethylether. The organic phase is washed successively with aqueous $NaHCO$, and with a NaCl-solution. After evaporation of the solvent 312 mg of a crystalline product is obtained. Recrystallization from diethylether yields 1α-hydroxy-previtamin $D_3$ of formula 30 (R=1.5-dimethylhexyl), with a melting-point of 120°–122° C.

UV ($CH_3OH$): $\lambda_{max}=260$ nm. The structure is established by means of its NMR spectrum.

EXAMPLE XI

Preparation of 1α,25-dihydroxy-vitamin $D_3$.

1 g of the adduct of 25-hydroxy-previtamin $D_3$ and 4-phenyl-1,2,4-triazoline-3,5-dione obtained as described in Example II (b), was converted by tert.-butyl-dimethylsilyl chloride to its 3-monosilyl ether in essentially the same way as described in Example VIII (b). Yield 1,1 g; melting-point 153° C.; $R_f$ (hexane/acetone:8/2)=0.28.

The above-described silylether was converted to the enone (formula 14, wherein R is a 1,5-dimethyl-5-hydroxyhexyl group) by the method described in Example VIII (c); UV: $\lambda_{max}=222$ nm, 242 nm; $R_f$ (hexane/acetone:7/3)=0.39; the NMR spectrum was in agreement with the desired structure. From the above silylether-enone the corresponding hydroxy-enone was prepared exactly as described in Example VIII (d); UV: $\lambda_{max}=223$ nm, 224 nm; $R_f$(hexane/acetone:6/4)=0.30. From the hydroxy-enone the corresponding dihydroxy-adduct was prepared exactly as described in Example VIII (e); UV: $\lambda_{max}=216$ nm; $R_f$ (hexane/acetone:7/3)=0.16; NMR spectrum identical with that of 1α-hydroxy adduct apart from extra 26,27-$CH_3$ signal at $\delta=1,22$. From the 1α-hydroxy adduct the desired 1α,25-dihydroxy-vitamin $D_3$ was prepared exactly as described in Example VIII (f). The structure of this final product was established by its NMR spectrum; UV: $\lambda_{max}=264$ nm; melting-point 106°–110° C.

We claim:

1. A method of preparing a 1α-hydroxyvitamin D or 1α-hydroxyprevitamin D compounds, characterized in that an adduct of a previtamin D compound and a dienophile, having the general formula:

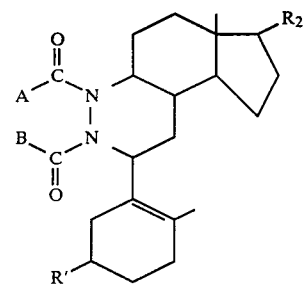

in which:

$R_2$ is a side chain derived from a compound selected from the group consisting of a previtamin D compound selected from the group consisting of previtamin $D_3$, 25-hydroxyprevitamin $D_3$, and 24,25- dihydroxyprevitamin D₃; the esterification product of a previtamin D compound selected from said group of previtamin D compounds and an esterification agent selected from the group consisting of alkylchlorocarbonates having 2 to 5 carbon atoms, aromatic carboxylic acids, saturated aliphatic carboxylic acids having 1 to 4 carbon atoms, p-toluenesulphonic acid, methane sulphonic acid, trifluoroacetic acid, and derivatives of said acids suitable for the esterification reaction; and the etherification product of a previtamin D compound selected from said group of previtamin D compounds and an etherification agent selected from the group consisting of triphenyl methyl halides, 2,3-dihydropyran, trialkylsilylhalides having 1 to 6 carbon atoms in the alkyl groups, and trialkylsilylethoxymethylhalides having 1 to 6 carbon atoms in the alkyl groups;

R' is selected from the group consisting of hydrogen, hydroxy, hydroxy esterified with an esterification agent selected from said group of esterification agents, and hydroxy etherified with an etherification agent selected from said group of etherification agents; and A and B independently represent alkoxy having 1 to 4 carbon atoms or jointly constitute a substituent selected from the group consisting of phenylimino and o-phenylene;

is hydroxylated in the 1α-position by a reaction with an oxidant selected from the group consisting of chromic acid, pyridine dichromate, tert.-butylchromate, bis(tetrabutylammonium) dichromate, chromiumtrioxide-3,5-dimethylpyrazole complex, and selenium dioxides, followed by reduction with a reductant selected from the group consisting of metal hydrides and complex metal hydrides; and subsequently, after removal of any protective ester or ether groups present, the 1α-hydroxyvitamin D or 1α-hydroxyprevitamin D compound is isolated.

2. A method as claimed in claim 1, characterized in that the starting substance used is an adduct of a previtamin D compound with 4-phenyl-1,2,4-triazoline-3,5-dione or 1,4-phthalazinedione.

3. A method as claimed in claim 1, characterized in that the starting substance used is an adduct of a previtamin D compound with dimethyl- or diethyl azodicarboxylate.

4. A method as claimed in claim 1, characterized in that the etherification agent used is a silyl compound selected from the group consisting of trimethylsilyl chloride, tert.-butyl dimethylsilylchloride and trimethylsilylethoxymethylchloride.

5. A method as claimed in claim 4, characterized in that the etherification agent used is selected from the group consisting of tert.-butyl dimethylsilylchloride and trimethylsilylchloride.

6. A method as claimed in claim 1, characterized in that the reduction agent used is the reaction product of lithiumaluminium hydride and aluminum chloride.

7. A method of preparing 1α-hydroxyvitamin D or 1α-hydroxyprevitamin D compounds, characterized in that an adduct of a previtamin D compound and a dienophile, having the general formula:

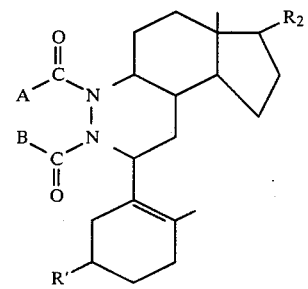

in which R₂, R', and A and B are as defined in claim 1, is hydroxylated in the 1α-position by a reaction with a brominating agent selected from the group consisting of N-bromosuccinimide, N,N'-dibromodimethylhydantoin and N-bromophthalimide, followed by hydrolysis; and subsequently, after removal of any protective ester or ether groups present, the 1α-hydroxyvitamin D or 1α-hydroxyprevitamin D compound is isolated.

8. A method as claimed in claim 7, characterized in that the starting substance used is an adduct of a previtamin D compound with 4-phenyl-1,2,4-triazoline-3,5-dione or 1,4-phthalazinedione.

9. A method as claimed in claim 7, characterized in that the starting substance used is an adduct of a previtamin D compound with dimethyl- or diethyl azodicarboxylate.

10. A method as claimed in claim 7, characterized in that the etherification agent used is a silyl compound selected from the group consisting of trimethylsilyl chloride, tert.-butyl dimethylsilylchloride and trimethylsilylethoxymethylchloride.

11. A method as claimed in claim 10, characterized in that the etherification agent used is selected from the group consisting of tert.-butyl dimethylsilylchloride and trimethylsilylchloride.

12. A method of preparing 1α-hydroxyvitamin D or 1α-hydroxyprevitamin D compounds, characterized in that an adduct of a previtamin D compound and a dienophile, having the general formula:

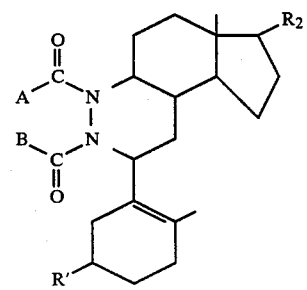

in which R₂, R', and A and B are as defined in claim 1; is hydroxylated in the 1α-position by a reaction with a brominating agent selected from the group consisting of N-bromosuccinimide, N,N'-dibromodimethylhydantoin and N-bromophthalimide, followed successively by oxidation with an oxidant selected from the group consisting of chromic acid, pyridine dichromate, tert.-butylchromate, bis(tetrabutylammonium)dichromate, chromiumtrioxide-3,5-dimethylpyrazole complex and manganese dioxide, and reduction with a reductant selected from the group consisting of metal hydrides and complex metal hydrides; and subsequently, after removal of any protective ester or ether groups present, the 1α-hydroxyvitamin D or 1α-hydroxyprevitamin D compound is isolated.

13. A method as claimed in claim 12, characterized in that the starting substance used is an adduct of a previtamin D compound with 4-phenyl-1,2,4-triazoline-3,5-dione or 1,4-phthalazinedione.

14. A method as claimed in claim 12, characterized in that the starting substance used is an adduct of a previtamin D compound with dimethyl- or diethyl azodicarboxylate.

15. A method as claimed in claim 12, characterized in that the etherification agent used is a silyl compound selected from the group consisting of trimethylsilyl chloride, tert.-butyl dimethylsilylchloride and trimethylsilylethoxymethylchloride.

16. A method as claimed in claim 15, characterized in that the etherification agent used is selected from the group consisting of tert.-butyl dimethylsilylchloride and trimethylsilylchloride.

17. A method as claimed in claim 12, characterized in that the reduction agent used is the reaction product of lithiumaluminium hydride and aluminum chloride.

18. A method of preparing 1α-hydroxyvitamin D or 1α-hydroxyprevitamin D compounds, characterized in that an adduct of a previtamin D compound and a dienophile, having the general formula:

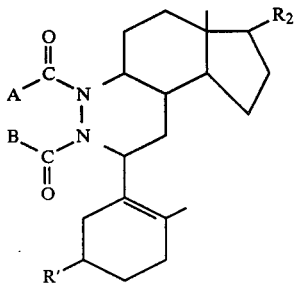

in which $R_2$, $R'$, and A and B are as defined in claim 1; is hydroxylated in the 1α-position by a reaction with a brominating agent selected from the group consisting of N-bromosuccinimide, N,N'-dibromodimethylhydantoin and N-bromophthalimide, followed by hydrolysis; followed successively by oxidation with an oxidant selected from the group consisting of chromic acid, pyridine dichromate, tert.-butylchromate, bis(tetrabutylammonium)dichromate, chromiumtrioxide-3,5-dimethylpyrazole complex and manganese dioxide, and reduction with a reductant selected from the group consisting of metal hydrides and complex metal hydrides; and subsequently after removal of any protective ester or ether groups present, the 1α-hydroxyvitamin D or 1α-hydroxyprevitamin D compound is isolated.

19. A method as claimed in claim 18, characterized in that the starting substance used is an adduct of a previtamin D compound with 4-phenyl-1,2,4-triazoline-3,5-dione or 1,4-phthalazinedione.

20. A method as claimed in claim 18, characterized in that the starting substance used is an adduct of a previtamin D compound with dimethyl- or diethyl azodicarboxylate.

21. A method as claimed in claim 18, characterized in that the etherification agent used is a silyl compound selected from the group consisting of trimethylsilyl chloride, tert.-butyl dimethylsilylchloride and trimethylsilylethoxymethylchloride.

22. A method as claimed in claim 21, characterized in that the etherification agent used is selected from the group consisting of tert.-butyl dimethylsilylchloride and trimethylsilylchloride.

23. A method as claimed in claim 18, characterized in that the reduction agent used is the reaction product of lithiumaluminium hydride and aluminum chloride.

24. A method of preparing a compound selected from the group consisting of 1α-hydroxyvitamin $D_3$, 1α-hydroxyprevitamin $D_3$, 1α,25-dihydroxyvitamin $D_3$, 1α,25-dihydroxyprevitamin $D_3$, 1α,24,25-trihydroxyvitamin $D_3$ and 1α,24,25-trihydroxyprevitamin $D_3$, characterized in that an adduct of a previtamin D compound and a dienophile, having the general formula:

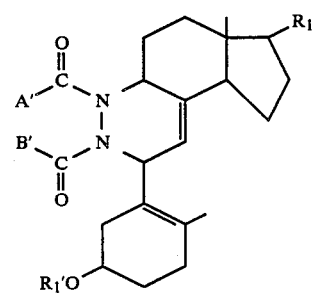

in which:
$R_1$ is a side chain derived from a previtamin D compound selected from the group consisting of previtamin $D_3$, 25-hydroxyprevitamin $D_3$, 24,25-dihydroxyprevitamin $D_3$, the etherification product of 25-hydroxyprevitamin $D_3$ and an etherification agent selected from the group consisting of tert.-butyl dimethylsilylchloride and trimethylsilylchloride, and the etherification product of 24,25-dihydroxyprevitamin $D_3$ and an agent selected from said group of etherification agents;
$R_1'$ is selected from the group consisting of tert.-butyl dimethylsilyl and trimethylsilyl; and
A' and B' are the same and are selected from the group consisting of methoxy and ethoxy, or together constitute a substituent selected from the group consisting of phenylimino and o-phenylene;
is hydroxylated in the 1α-position by a reaction with an oxidant selected from the group consisting of chromic acid, pyridine dichromate and chromiumtrioxide-3,5-dimethylpyrazole, followed by reduction with the reaction product of lithium aluminum hydride and aluminum chloride; and subsequently, after removal of the tert.-butyl dimethylsilyl group or the trimethylsilyl group by means of treatment with a fluorine-containing compound or a mineral acid, respectively, and after removal of the dienophile group by means of treatment with potassium hydroxide in a lower aliphatic alcohol, the 1α-hydroxyvitamin D or 1α-hydroxyprevitamin D compound is isolated.

25. A method as claimed in claimed in claim 24, characterized in that prior to the isolation of the 1α-hydroxyvitamin D or 1α-hydroxyprevitamin D compound, the hydroxylated vitamin D or previtamin D compound is oxidized by manganese dioxide and subsequently stereospecifically reduced by the reaction product of lithium aluminum hydride and aluminum chloride.

26. A method of preparing a compound selected from the group consisting of 1α-hydroxyvitamin $D_3$, 1α-hydroxyprevitamin $D_3$, 1α,25-dihydroxyvitamin $D_3$, 1α,25-dihydroxyprevitamin $D_3$, 1α,24,25-trihydroxyvitamin $D_3$ and 1α,24,25-trihydroxyprevitamin $D_3$, characterized in that an adduct of a previtamin D compound and a dienophile, having the general formula:

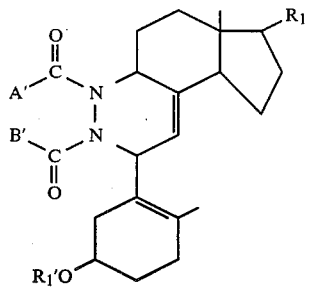

in which:
R$_1$ is a side chain derived from a previtamin D compound selected from the group consisting of previtamin $D_3$, 25-hydroxyprevitamin $D_3$, 24,25-dihydroxyprevitamin $D_3$, the etherification product of 25-hydroxyprevitamin $D_3$ and an etherification agent selected from the group consisting of tert.-butyl dimethylsilylchloride and trimethylsilylchloride, and the etherification product of 24,25-dihydroxyprevitamin $D_3$ and an agent selected from said group of etherification agents;
R$_1'$ is selected from the group consisting of tert.-butyl dimethylsilyl and trimethylsilyl; and
A' and B' are the same and are selected from the group consisting of methoxy and ethoxy, or together constitute a substituent selected from the group consisting of phenylimino and o-phenylene;
is hydroxylated in the 1α-position by a reaction with a brominating agent selected from the group consisting of N-bromosuccinimide, N,N'-dibromodimethylhydantoin and N-bromophthalimide, followed by hydrolysis; and subsequently, after removal of the tert.-butyl dimethylsilyl group or the trimethylsilyl group by means of treatment with a fluorine-containing compound or a mineral acid, respectively, and after removal of the dienophile group by means of treatment with potassium hydroxide in a lower aliphatic alcohol, the 1α-hydroxyvitamin D or 1α-hydroxyprevitamin D compound is isolated.

27. A method as claimed in claim 26, characterized in that prior to the isolation of the 1α-hydroxyvitamin D or 1α-hydroxyprevitamin D compound, the hydroxylated vitamin D or previtamin D compound is oxidized by manganese dioxide and subsequently stereospecifically reduced by the reaction product of lithium aluminum hydride and aluminum chloride.

28. A method of preparing a compound selected from the group consisting of 1α-hydroxyvitamin $D_3$, 1α-hydroxyprevitamin $D_3$, 1α,25-dihydroxyvitamin $D_3$, 1α,25-dihydroxyprevitamin $D_3$, 1α,24,25-trihydroxyvitamin $D_3$ and 1α,24,25-trihydroxyprevitamin $D_3$, characterized in that an adduct of a previtamin D compound and a dienophile, having the general formula:

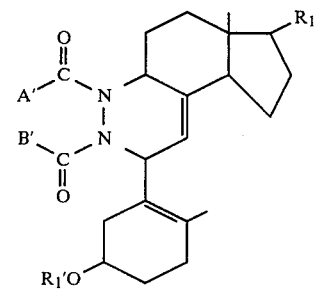

in which:
R$_1$ is a side chain derived from a previtamin D compound selected from the group consisting of previtamin $D_3$, 25-hydroxyprevitamin $D_3$, 24,25-dihydroxyprevitamin $D_3$, the etherification product of 25-hydroxyprevitamin $D_3$ and an etherification agent selected from the group consisting of tert.-butyl dimethylsilylchloride and trimethylsilylchloride, and the etherification product of 24,25-dihydroxyprevitamin $D_3$ and an agent selected from said group of etherification agents;
R$_1'$ is selected from the group consisting of tert.-butyl dimethylsilyl and trimethylsilyl; and
A' and B' are the same and are selected from the group consisting of methoxy and ethoxy, or together constitute a substituent selected from the group consisting of phenylimino and o-phenylene; is hydroxylated in the 1α-position by a reaction with an brominating agent selected from the group consisting of N-bromosuccinimide, N,N'-dibromodimethylhydantoin and N-bromophthalimide, followed by oxidation with an oxidant selected from the group consisting of pyridine-dichromate and bis(tetrabutylammonium)dichromate and stereospecific reduction with the reaction product of lithium aluminum hydride and aluminum chloride; and subsequently, after removal of the tert.-butyl dimethylsilyl group or the trimethylsilyl grou by means of treatment with a fluorine-containing compound or a mineral acid, respectively, and after removal of the dienophile group by means of treatment with potassium hydroxide in a lower aliphatic alcohol, the 1α-hydroxyvitamin D or 1α-hydroxyprevitamin D compound is isolated.

29. A method as claimed in claim 28, characterized in that prior to the isolation of the 1α-hydroxyvitamin D or 1α-hydroxyprevitamin D compound, the hydroxylated vitamin D or previtamin D compound is oxidized by manganese dioxide and subsequently stereospecifically reduced by the reaction product of lithium aluminum hydride and aluminum chloride.

30. A method of preparing a compound selected from the group consisting of 1α-hydroxyvitamin $D_3$, 1α-hydroxyprevitamin $D_3$, 1α,25-dihydroxyvitamin $D_3$, 1α,25-dihydroxyprevitamin $D_3$, 1α,24,25-trihydroxyvitamin $D_3$ and 1α,24,25-trihydroxyprevitamin $D_3$, characterized in that an adduct of a previtamin D compound and a dienophile, having the general formula:

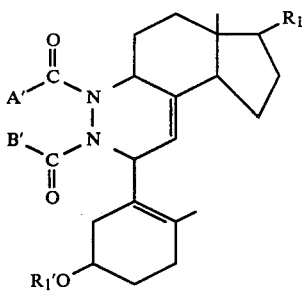

in which:
R₁ is a side chain derived from a previtamin D compound selected from the group consisting of previtamin $D_3$, 25-hydroxyprevitamin $D_3$, 24,25-dihydroxyprevitamin $D_3$, the etherification product of 25-hydroxyprevitamin $D_3$ and an etherification agent selected from the group consisting of tert.-butyl dimethylsilylchloride and trimethylsilylchloride, and the etherification product of 24,25-dihydroxyprevitamin $D_3$ and an agent selected from said group of etherification agents;

$R_1'$ is selected from the group consisting of tert.-butyl dimethylsilyl and trimethylsilyl; and A' and B' are the same and are selected from the group consisting of methoxy and ethoxy, or together constitute a substituent selected from the group consisting of phenylimino and o-phenylene; is hydroxylated in the 1α-position by an oxidation reaction with an oxidant selected from the group consisting of chromic acid, pyridine dichromate and manganese dioxide, followed by reduction with the reaction product of lithium aluminum hydride and aluminum chloride, said adduct having been hydroxylated in the 1α-position prior to the oxidation reaction by reaction with a brominating agent selected from the group consisting of N-bromosuccinimide, N,N'-dibromodimethylhydantoin and N-bromophthalimide followed by hydrolysis; and subsequently, after removal of the tert.-butyl dimethylsilyl group or the trimethylsilyl group by means of treatment with a fluorine-containing compound or a mineral acid, respectively, and after removal of the dienophile group by means of treatment with potassium hydroxide in a lower aliphatic alcohol, the 1α-hydroxyvitamin D or 1α-hydroxyprevitamin D compound is isolated.

31. An adduct of a previtamin D or tachysterol compound and a dienophile, having the general formula:

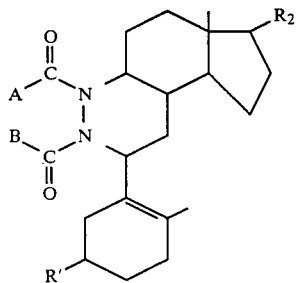

in which:
R' is selected from the group consisting of hydrogen, hydroxy, hydroxy esterified with an esterification agent selected from the group of esterification agents identified in claim 1, and hydroxy etherified with an etherification agent selected from the group of etherification agents identified in claim 1;

A' and B' are the same and are selected from the group consisting of methoxy and ethoxy, or together constitute a substituent selected from the group consisting of phenylimino and o-phenylene; and $R_2$ is a side chain derived from a compound selected from the group consisting of a previtamin D compound selected from the group consisting of previtamin $D_3$, 25-hydroxyprevitamin $D_3$, and 24,25-dihydroxyprevitamin $D_3$; the esterification product of a previtamin D compound selected from said group of previtamin D compounds and an esterification agent selected from the group of esterification agents identified in claim 1; and the etherification product of a previtamin D compound selected from said group of previtamin D compounds and an etherification agent selected from the group of etherification agents identified in claim 1.

32. A method of preparing the adduct claimed in claim 31, characterized in that the adduct is prepared by reacting a previtamin D compound of the formula:

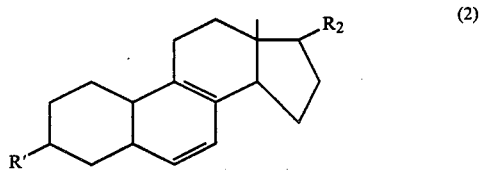

(2)

in which:
$R_2$ is a side chain derived from a compound selected from the group consisting of a previtamin D compound selected from the group consisting of previtamin $D_3$, 25-hydroxyprevitamin $D_3$, and 24,25-dihydroxyprevitamin $D_3$; the esterification product of a previtamin D compound selected from said group of previtamin D compounds and an esterification agent selected from the group consisting of alkylchlorocarbonates having 2 to 5 carbon atoms, aromatic carboxylic acids, saturated aliphatic carboxylic acids having 1 to 4 carbon atoms, p-toluenesulphonic acid, methane sulphonic acid, trifluoroacetic acid, and derivatives of said acids suitable for the esterification reaction; and the etherification product of a previtamin D compound selected from said group of previtamin D compounds and an etherification agent selected from the group consisting of triphenyl methyl halides, 2,3-dihydropyran, trialkylsilylhalides having 1 to 6 carbon atoms in the alkyl groups, and trialkylsilylethoxymethylhalides having 1 to 6 carbon atoms in the alkyl groups; and R' is selected from the group consisting of hydrogen, hydroxy, hydroxy esterified with an esterification agent selected from said group of esterification agents, and hydroxy etherified with an etherification agent selected from said group of etherification agents; with a dienophile of the formula:

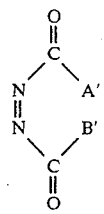

(3)

in which:
A' and B' are the same and are selected from the group consisting of methoxy and ethoxy, or together constitute a substituent selected from the group consisting of phenylimino and o-phenylene; in an inert organic solvent at room temperatur or at a slightly reduced temperature.

33. A method of preparing the adduct claimed in claim 31, characterized in that the adduct is prepared by reacting a tachysterol compound of the formula:

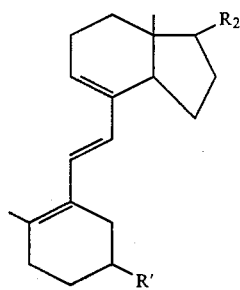

(2a)

in which:
$R_2$ in a side chain derived from a compound selected from the group consisting of a previtamin D compound selected from the group consisting of previtamin $D_3$, 25-hydroxyprevitamin $D_3$, and 24,25-dihydroxyprevitamin $D_3$; the esterification product of a previtamin D compound selected from said group of previtamin D compounds and an esterification agent selected from the group consisting of alkylchlorocarbonates having 2 to 5 carbon atoms, aromatic carboxylic acids, saturated aliphatic carboxylic acids having 1 to 4 carbon atoms, p-toluenesulphonic acid, methane sulphonic acid, trifluoroacetic acid, and derivatives of said acids suitable for the esterification reaction; and the etherification product of a previtamin D compound selected from said group of previtamin D compounds and an etherification agent selected from the group consisting of triphenyl methyl halides, 2,3-dihydropyran, trialkylsilylhalides having 1 to 6 carbon atoms in the alkyl groups, and trialkylsilylethoxymethylhalides having 1 to 6 carbon atoms in the alkyl groups; and R' is selected from the group consisting of hydrogen, hydroxy, hydroxy esterified with an esterification agent selected from said group of esterification agents, and hydroxy etherified with an etherification agent selected from said group of etherification agents; with a dienophile of the formula:

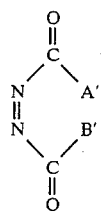

(3)

in which:
A' and B' are the same and are selected from the group consisting of methoxy and ethoxy, or together constitute a substituent selected from the group consisting of phenylimino and o-phenylene; in an inert organic solvent at room temperature or at a slightly reduced temperature.

34. A method of preparing the adduct of a previtamin D compound claimd in claim 31, characterized in that the adduct is prepared by subjecting a 7-dehydrocholesterol compound of the formula:

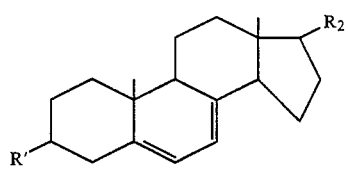

in which:
$R_2$ in a side chain derived from a compound selected from the group consisting of a previtamin D compound selected from the group consisting of previtamin $D_3$, 25-hydroxyprevitamin $D_3$, and 24,25-dihydroxyprevitamin $D_3$; the esterification product of a previtamin D compound selected from said group of previtamin D compounds and an esterification agent selected from the group consisting of alkylchlorocarbonates having 2 to 5 carbon atoms, aromatic carboxylic acids, saturated aliphatic carboxylic acids having 1 to 4 carbon atoms, p-toluenesulphonic acid, methane sulphonic acid, trifluoroacetic acid, and derivatives of said acids suitable for the esterification reaction; and the etherification product of a previtamin D compound selected from said group of previtamin D compounds and an etherification agent selected from the group consisting of triphenyl methyl halides, 2,3-dihydropyran, trialkylsilylhalides having 1 to 6 carbon atoms in the alkyl groups, and trialkylsilylethoxymethylhalides having 1 to 6 carbon atoms in the alkyl groups; and R' is selected from the group consisting of hydrogen, hydroxy, hydroxy esterified with an esterification agent selected from said group of esterification agents, and hydroxy etherified with an etherification agent selected from said group of etherification agents; to UV-irradiation in an inert organic solvent at room temperature or at a slightly reduced temperature and, after recovering the nonconverted starting material, reacting the product obtained with a dienophile of the formula:

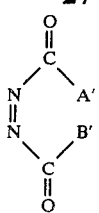
(3) in which:
A' and B' are the same and are selected from the group consisting of methoxy and ethoxy, or together constitute a substituent selected from the group consisting of phenylimino and o-phenylene; in an inert organic solvent at the same temperature as the temperature utilized for the irradiation reaction.
* * * * *

UNITED STATES PATENT AND TRADEMARK OFFICE
CERTIFICATE OF CORRECTION

PATENT NO. : 4,539,153
DATED : September 3, 1985
INVENTOR(S) : VANDEWALLE, et al.

It is certified that error appears in the above-identified patent and that said Letters Patent is hereby corrected as shown below:

Column 5, lines 37/38 change "sutiable to -- suitable --.

Column 6, lines 19/20 change "3,6-transvitamin " to -- 5,6-transvitamin".

Column 7, line 25, change "esterifification" to -- esterification".

Column 11, line 55, change "1 -hydroxyvitamin $R_3$" to --1 -hydroxyvitamin $D_3$--.

Column 17, line 36, change "selenium dioxides" to --selenium dioxide--.

UNITED STATES PATENT AND TRADEMARK OFFICE
CERTIFICATE OF CORRECTION

PATENT NO. : 4,539,153

DATED : September 3, 1985

INVENTOR(S) : VANDEWALLE, et al.

It is certified that error appears in the above-identified patent and that said Letters Patent is hereby corrected as shown below:

Column 22, line 45, change "grou" to --group--.

Column 25, line 38, change "in" to --is--.

Column 26, line 20, change "claimd" to --claimed--.

UNITED STATES PATENT AND TRADEMARK OFFICE
CERTIFICATE OF CORRECTION

PATENT NO.  : 4,539,153
DATED       : September 3, 1985
INVENTOR(S) : VANDEWALLE, et al.

It is certified that error appears in the above-identified patent and that said Letters Patent is hereby corrected as shown below:

On formula sheet number 3 please substitute the following formulas:

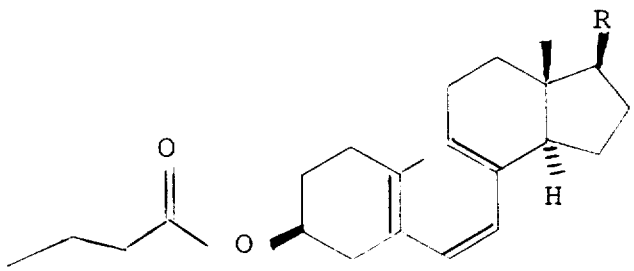

Formula (7).

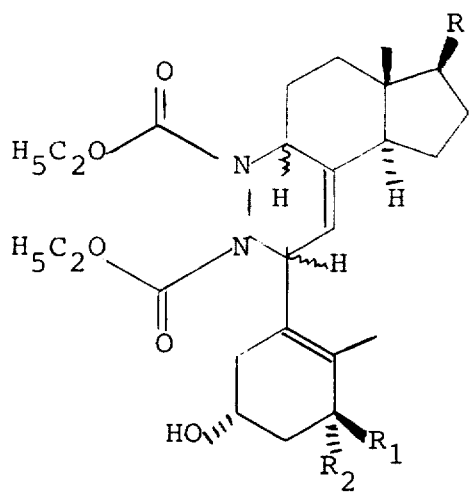

Formula (25) and (26).

UNITED STATES PATENT AND TRADEMARK OFFICE
CERTIFICATE OF CORRECTION

PATENT NO. : 4,539,153  
DATED : September 3, 1985  
INVENTOR(S) : VANDEWALLE, et al.

Page 4 of 7

It is certified that error appears in the above-identified patent and that said Letters Patent is hereby corrected as shown below:

On formula sheet Number 3 change the following formula:

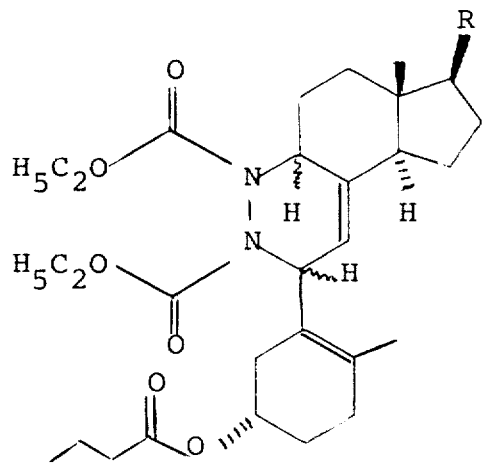

Formula (20).

UNITED STATES PATENT AND TRADEMARK OFFICE
CERTIFICATE OF CORRECTION

PATENT NO. : 4,539,153

DATED : September 3, 1985

INVENTOR(S) : VANDEWALLE, et al.

It is certified that error appears in the above-identified patent and that said Letters Patent is hereby corrected as shown below:

Please substitute the following formula in claims 1, 7, 12 and 18:

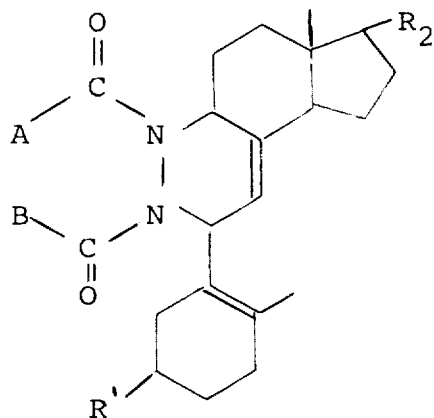

UNITED STATES PATENT AND TRADEMARK OFFICE
CERTIFICATE OF CORRECTION

PATENT NO. : 4,539,153

DATED : September 3, 1985

INVENTOR(S) : VANDEWALLE, et al.

It is certified that error appears in the above-identified patent and that said Letters Patent is hereby corrected as shown below:

Please substitute the following formula in claim 31:

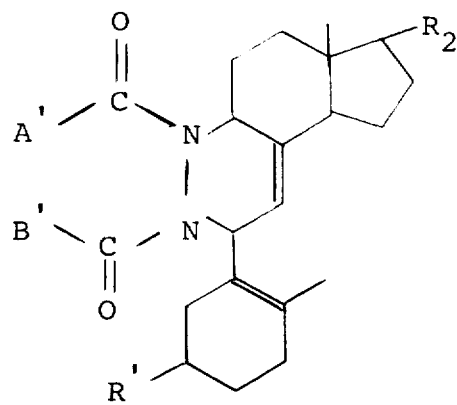

UNITED STATES PATENT AND TRADEMARK OFFICE
CERTIFICATE OF CORRECTION

PATENT NO. : 4,539,153

DATED : September 3, 1985

INVENTOR(S) : VANDEWALLE, et al.

It is certified that error appears in the above-identified patent and that said Letters Patent is hereby corrected as shown below:

Please substitute the following formula in claim 32:

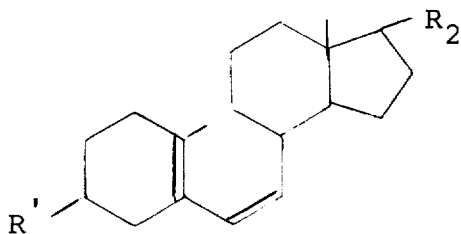

Signed and Sealed this

Seventh Day of January 1986

[SEAL]

Attest:

DONALD J. QUIGG

Attesting Officer

Commissioner of Patents and Trademarks